United States Patent [19]

Yamada et al.

[11] Patent Number: 4,900,672

[45] Date of Patent: Feb. 13, 1990

[54] METHOD FOR PRESERVATION OF NITRILE HYDRATION ACTIVITY

[75] Inventors: Hideaki Yamada, Kyoto; Kanehiko Enomoto, Tokyo; Koitchiro Ryuno; Hitoshi Shimizu, both of Yokohama, all of Japan

[73] Assignee: Nitto Kagaku Kogyo Kabushiki Kaisha, Tokyo, Japan

[21] Appl. No.: 45,870

[22] Filed: May 1, 1987

[30] Foreign Application Priority Data

May 2, 1986 [JP] Japan ................................. 61-101043

[51] Int. Cl.$^4$ .............................................. C12N 9/96
[52] U.S. Cl. ...................................... 435/188; 435/227
[58] Field of Search ................................. 435/188, 227

[56] References Cited

U.S. PATENT DOCUMENTS 4,390,631 6/1983 Watanabe et al. .................... 435/227
4,629,700 12/1986 Prevatt et al. ......................... 435/227

FOREIGN PATENT DOCUMENTS 0115781 8/1984 European Pat. Off. ............ 435/227
0137076 4/1985 European Pat. Off. ............ 435/227

OTHER PUBLICATIONS

Bui et al., "A Note on the Enzymic Action and Biosynthesis of a Nitrile-Hydratase from a Brevibacterium Sp.", J. Appl. Bacteriol. 1984, 57(1), 183–190.

Fradet et al., "Hydratation of Nitriles Using a Bacterial Nitrile-Hydratase Immobilized on DEAE-Cellulose," Biotech. and Bioeng., vol. 27, No. 11, pp. 1581–1585 (1985).

Nagasawa et al., "Nitrile Hydratase of Pseudomonas Chlororaphis B23," Eur. J. Biochem. 162, 691–698 (Feb. 1987).

*Primary Examiner*—Robert A. Wax
*Attorney, Agent, or Firm*—Emmanuel J. Lobato; Robert E. Burns

[57] ABSTRACT

Nitrile hydration activity of nitrile hydratase produced by a microorganism of the genus Pseudomonas or Pseudomonas microorganism cells per se or in the immobilized state, all having nitrile hydration activity can be stably preserved by adding as a stabilizer at least one compound selected from nitriles, amides, and organic acids and salts thereof to a suspension or solution of the nitrile hydratase, or the microorganism cells per se or in the immobilized state.

5 Claims, No Drawings

METHOD FOR PRESERVATION OF NITRILE HYDRATION ACTIVITY

BACKGROUND OF THE INVENTION

The present invention relates to a method for prevention of reduction with elapse of time in nitrile hydration activity of nitrile hydratase produced by a microorganism of the genus Pseudomonas and for stable preservation of this activity.

In recent years, the technology of immobilized enzymes and microorganisms has developed rapidly, resulting in increasing attempts to utilize microorganisms and enzymes as they are or in the immobilized state as catalysts for various single or complex chemical reactions.

Nitrile hydratase was discovered by Hideaki Yamada, one of the present inventors, et al., as an enzyme capable of hydrating nitriles to produce the corresponding amides. (Reference: Agric. Biol. Chem. 46, 1165–1174 (1982)) As one example of the utilization of this enzyme, a method for producing from $C_{2-4}$ nitriles the corresponding amides with the use of Pseudomonas microorganisms which produce nitrile hydratase has been proposed. (References: U.S. Pat. No. 4,637,982 and Agric. Biol. Chem. 46, 1183–1189 (1982))

As a result of further investigation, we have found that the nitrile hydration activity of the above-mentioned nitrile hydratase is labile and decreases with elapse of time. This decrease occurs in either case where the nitrile hydratase stays in microorganism cells or is separated from the cells irrespective of whether or not immobilization is effected, but the separated enzyme shows a greater reduction in nitrile hydration activity and even becomes quite unusable within a short period of time when the reduction is drastic.

SUMMARY OF THE INVENTION

As a result of extensive research effort expended toward solving the above problems and efficiently utilizing the nitrile hydration activity of nitrile hydratase, we have found that the use of nitriles, amides and organic acids or salts thereof is very effective for this purpose and have arrived at the present invention on the basis of this finding.

More specifically, the present invention provides a method for preservation of the nitrile hydration activity of nitrile hydratase produced by a microorganism of the genus Pseudomonas, of cells of microorganisms of said genus Pseudomonas, or of immobilized forms thereof, all having nitrile hydration activity, which method comprises adding as a stabilizer at least one compound selected from the group consisting of nitriles, amides, and organic acids and salts thereof to a suspension or solution of said nitrile hydratase, of said microorganism cells, or of said immobilized forms thereof.

DETAILED DESCRIPTION OF THE INVENTION

Microorganism

The microorganisms used in the present invention are those of the genus Pseudomonas capable of producing nitrile hydratase and hydrating nitriles, especially acrylonitrile, to produce the corresponding amides, especially acrylamide. Specific examples of such microorganisms are *Pseudomonas chlororaphis* B 23 (FERM BP-187) and Pseudomonas sp. PS 1 (FERM BP-188) disclosed in Japanese Patent Pub. No. 37951/1984 mentioned above, and *Pseudomonas ovalis* (IAM 1002), *Pseudomonas fluorescens* (IFO 3081 and IFO 3925) and *Pseudomonas reptilivora* (IFO 3461) listed in JFCC Catalogue of Cultures, Third Ed. (1979). These microorganisms were deposited with the Fermentation Research Institute, Agency of Industrial Science & Technology (FERM), the Tokyo University Institute of Applied Microbiology (IAM) and the Institute of Fermentation, Incorporated Foundation (IFO) and accorded respectively the above accession numbers.

Cultivation of these microorganisms is ordinarily carried out under aerobic conditions by inoculating strains of the respective microorganisms into culture media containing: carbon sources such as glucose, sucrose, dextrins, and glycerol; nitrogen sources such as ammonium sulfate and urea; organic nutrient sources such as yeast extract, meat extract, malt extract, and peptone; enzyme inducers such as propionitrile, isobutyronitrile, propionamide, isobutyramide, and methacrylamide and other optional ingredients.

The pH of the culture medium is of the order of 6 to 9, preferably of the order of 7 to 8, while the cultivation temperature is of the order of 20° to 37° C., preferably of the order of 20° to 30° C., and the cultivation time is about 1 to 3 days. Cells obtained by the cultivation can be collected, for example, by centrifugation.

Nitrile Hydratase

The nitrile hydratase used in the present invention is an enzyme produced by the aforementioned microorganism and can be separated and extracted by the following procedure.

First, the cells collected from the culture fluid by centrifugation and the like are suspended in a buffer in a quantity sufficient to reach a given cell concentration and crushed in an ultrasonic cell crusher, Daino mill or French press. Uncrushed cells and cell walls or membranes are removed, for example, by centrifugation to obtain a soluble fraction (cell extract). The cell extract thus obtained is purified by a conventional method such as ammonium sulfate fractionation, DEAE-Sephacel Phenyl-Sepharose ® or Sephadex ® column chromatography, or crystallization whereby a partly purified enzyme solution or a purified enzyme (solution) can be obtained.

Both these enzymes can be used in the present invention irrespective of whether they are purified partly or completely.

Immobilized Cell.Immobilized Enzyme

The immobilized cells and enzymes of the present invention can be obtained by subjecting the above stated microorganism cells and nitrile hydratase to the adsorption method which involves absorption onto activated carbon and the like, the ionic bond method which involves bonding to ion exchange resins and the like, the covalently bonding method which involves covalently bonding to glass beads, and the entrapping method which involves entrapping with acrylamide, carrageenan, alginate and the like in accordance with a conventional method.

Stabilizer

The stabilizers used in the present invention are compounds selected from nitriles, amides, and organic acids and salts thereof, and these compounds can be used singly or in combination.

Specific examples of such compounds are:

(1) Aliphatic nitriles such as acetonitrile, propionitrile and isobutyronitrile and the corresponding amides and acids or salts thereof.

(2) Aminonitriles such as glycine nitrile, α-aminopropionitrile and β-aminopropionitrile and the corresponding amides and acids or salts thereof.

(3) Hydroxynitriles such as lactonitrile, hydroxyacetonitrile and β-hydroxypropionitrile and the corresponding amides and acids or salts thereof.

(4) Unsaturated nitriles such as acrylonitrile and methacrylonitrile and the corresponding amides and acids or salts thereof.

(5) Dinitriles such as malononitrile, succinonitrile and adiponitrile and the corresponding diamides and dibasic acids or salts thereof.

(6) Monocyanoamides and monocyanic acids such as cyanoacetamide and cyanoacetic acid or salts thereof.

(7) Aromatic nitriles such as benzonitrile and phenylacetonitrile and the corresponding amides and acids or salts thereof.

(8) Heterocyclic nitriles such as nicotinonitrile and isonicotinonitrile and the corresponding amides and acids or salts thereof.

(9) Halogenated nitriles such as chloroacetonitrile and β-chloropropionitrile and the corresponding amides and acids or salts thereof.

(10) Acides having an aldehyde group such as glyoxylic acid or salts thereof.

Preservation of Nitrile Hydration Activity

The preservation of nitrile hydration activity can be attained by adding any of the above enumerated compounds to a suspension or solution of the previously mentioned microorganism cells and nitrile hydratase as they are or in an immobilized state dispersed or dissolved in various buffers or physiological saline. Ordinarily, the quantity of the stabilizer added is in the range of from 0.01 to 50 g/l but 0.1 to 10 g/l of the stabilizer is preferably added from the point of view of storage stability, cost and the like.

The pH of the suspension or solution is 5 to 8, preferably 5.5 to 7, and a variety of buffers such as phosphate buffer and Tris buffer are ordinarily employed. In some cases, it may be effective to control pH by adding an acid such as hydrochloric acid or sulfuric acid or an alkali such as caustic soda or caustic potash.

While the suspension or solution thus obtained may be stored at room temperature as long as the storage period is short, storage at a low temperature, especially at a temperature in the vicinity of 0° C. is preferred.

In accordance with the present invention, nitrile hydration activity can be preserved stably over a long period of time. The addition of the stabilizer of the present invention is particularly effective for enzymes separation from microorganism cells and liable to show a substantial reduction in activity with elapse of time. This effect is observed not only in the storage stability of the enzyme solution at the respective stages of the enzyme purification described previously but also in the preservation of the enzyme activity in each purification step. It is therefore preferable that the stabilizer be added to the enzyme solution or buffer used in each purification step.

In order to indicate more fully the nature and utility of this invention, the following specific examples of practice are set forth, it being understood that these examples are presented as illustrative only and not intended to limit the scope of the invention.

EXPERIMENTAL EXAMPLES

In each of the following experimental examples, 0.1 ml of an enzyme solution or cell suspension was added to 9.9 ml of M/20 phosphate buffer (pH 7.7) containing 2.5% by weight of acrylonitrile, and the resulting solution was caused to react at 10° C. for 10 minutes. The nitrile hydration activity of the test samples was determined by measuring the quantity of acrylamide produced by gas chromatography, the capability of producing 1μ mole of acrylamide per ml of the enzyme solution or cell suspension per minute being designated as 1 unit (U).

EXAMPLES 1 THROUGH 21 AND COMPARISON EXAMPLE 1

Culture media each comprising 10 g/l of sucrose, 1 g/l of $KH_2PO_4$, 1 g/l of $K_2HSO_4$, 1 g/l of $MgSO_4.7H_2O$, 10 g/l of chemical soy sauce, 1 g/l of L-cysteine, 10 g/l of $FeSO_4.7H_2O$, and 8 g/l of methacrylamide were adjusted to a pH of 7.2, and 100 ml of each resulting culture medium was sterilized in a 500-ml Erlenmeyer flask.

After cooling, each sterilized culture medium was inoculated with 1 ml of a culture fluid obtained by pre-cultivating *Pseudomonas chlororaphis* B23 (FERM BP-187) in a culture medium (pH 7.8) comprising 5 g/l of sucrose, 5 g/l of peptone, 3 g/l of yeast extract, and 3 g/l of malt extract for one day, and cultivation was carried out aerobically at 25° C. for 2 days.

Cells were separated from the culture fluid by centrifugation (3° C., 10,000 rpm, 20 minutes) and washed with a physiological saline. The washed cells were subjected to centrifugation under the same conditions and then suspended in a physiological saline to obtain a suspension of washed cells (cell concentration: c.a. 20 g/l, $1.7 \times 10^3$ U/ml).

To 2.5 ml of this cell suspension was added 2.5 ml of M/10 phosphate buffer containing 10 mg of each of the nitriles shown in Table 1, the pH of the cell suspension was adjusted to 6.5, and then the cell suspension was left standing for 5 days in ice-cooled state. The residual nitrile hydration activity percent (in Table 1, as in all succeeding tables, abbreviated to % residual activity) was calculated on the basis of the nitrile hydration activity levels measured before and after the cell suspension was left standing. The results obtained are summarized in Table 1 below.

TABLE 1

| Experimental Example | Nitrile Added | % Residual Activity |
| --- | --- | --- |
| Comparison Example 1 | None | 42 |
| Example | | |
| 1 | Acetonitrile | 71 |
| 2 | Propionitrile | 90 |
| 3 | n-Butyronitrile | 88 |
| 4 | Isobutyronitrile | 95 |
| 5 | n-Valeronitrile | 93 |
| 6 | n-Capronitrile | 89 |
| 7 | Glycine nitrile | 68 |
| 8 | β-Aminopropionitrile | 70 |
| 9 | Lactonitrile | 73 |
| 10 | β-Hydroxypropionitrile | 84 |
| 11 | Acrylonitrile | 71 |
| 12 | Methacrylonitrile | 80 |
| 13 | Malononitrile | 69 |
| 14 | Succiononitrile | 81 |

TABLE 1-continued

| Experimental Example | Nitrile Added | % Residual Activity |
|---|---|---|
| 15 | Adiponitrile | 84 |
| 16 | Cyanoacetamide | 75 |
| 17 | Cyanoacetic acid | 69 |
| 18 | Benzonitrile | 70 |
| 19 | Nicotinonitrile | 73 |
| 20 | Chloroacetonitrile | 77 |
| 21 | β-Chloropropionitrile | 80 |

EXAMPLES 22 THROUGH 39 AND COMPARISON EXAMPLE 2

The procedures of Examples 1 through 21 were followed except that the nitriles added were replaced by amides, whereupon the results shown in Table 2 were obtained.

TABLE 2

| Experimental Example | Amide Added | % Residual Activity |
|---|---|---|
| Comparison Example 2 | None | 42 |
| Example | | |
| 22 | Acetamide | 67 |
| 23 | Propionamide | 93 |
| 24 | n-Butyramide | 89 |
| 25 | Isobutyramide | 99 |
| 26 | n-Valeramide | 94 |
| 27 | n-Capronamide | 88 |
| 28 | Glycine amide | 63 |
| 29 | β-Aminopropionamide | 68 |
| 30 | Lactamide | 70 |
| 31 | β-Hydroxypropionamide | 74 |
| 32 | Acrylamide | 73 |
| 33 | Methacrylamide | 79 |
| 34 | Malondiamide | 66 |
| 35 | Succindiamide | 68 |
| 36 | Benzamide | 65 |
| 37 | Nicotinamide | 59 |
| 38 | Chloroacetamide | 71 |
| 39 | β-Chloropropionamide | 71 |

EXAMPLES 40 THROUGH 59 AND COMPARISON EXAMPLE 3

The procedures of Examples 1 through 21 were followed except that the nitriles added were replaced by organic acids and that the pH of each cell suspension was adjusted to 6.0. The results obtained are set forth in Table 3.

TABLE 3

| Experimental Example | Organic Acid Added | % Residual Activity |
|---|---|---|
| Comparison Example 3 | None | 43 |
| Example | | |
| 40 | Formic Acid | 83 |
| 41 | Acetic acid | 77 |
| 42 | Propionic acid | 93 |
| 43 | Isobutyric acid | 97 |
| 44 | Valeric acid | 84 |
| 45 | Caproic acid | 83 |
| 46 | β-Aminopropionic acid | 71 |
| 47 | Malic acid | 81 |
| 48 | Citric acid | 77 |
| 49 | Fumaric acid | 82 |
| 50 | Glycolic acid | 77 |
| 51 | DL-Glyceric acid | 87 |
| 52 | Oxalacetic acid | 83 |
| 53 | Succinic acid | 80 |
| 54 | Malonic acid | 63 |
| 55 | Benzoic acid | 68 |

TABLE 3-continued

| Experimental Example | Organic Acid Added | % Residual Activity |
|---|---|---|
| 56 | Monochloroacetic acid | 70 |
| 57 | Glyoxylic acid | 88 |
| 58 | Acrylic acid | 70 |
| 59 | Methacrylic acid | 81 |

EXAMPLES 60 THROUGH 77 AND COMPARISON EXAMPLES 4

To each 2.5-ml aliquot of a suspension of washed cells ($1.8 \times 10^3$ U/ml) prepared as in Example 1, was added 2.5 ml of M/10 phosphate buffer containing 25 mg of a stabilizer as shown in Table 4. The pH of the mixture was adjusted to a predetermined level, and the resulting mixture was then left standing for 4 days in ice-cooled state.

The nitrile hydration activity levels were measured before and after each of the suspensions was left standing to calculate % residual activity, whereupon the results summarized in Table 4 were obtained.

TABLE 4

| Experimental Example | Stabilizer Added | pH | % Residual Activity |
|---|---|---|---|
| Comparison Example | | | |
| 4 | None | 5.0 | 2 |
| 5 | " | 5.5 | 32 |
| 6 | " | 6.0 | 41 |
| 7 | " | 6.5 | 52 |
| 8 | " | 7.0 | 43 |
| 9 | " | 8.0 | 26 |
| Example | | | |
| 60 | Isobutyronitrile | 5.0 | 5 |
| 61 | " | 5.5 | 98 |
| 62 | " | 6.0 | 97 |
| 63 | " | 6.5 | 85 |
| 64 | " | 7.0 | 80 |
| 65 | " | 8.0 | 53 |
| Example | | | |
| 66 | Isobutyramide | 5.0 | 3 |
| 67 | " | 5.5 | 100 |
| 68 | " | 6.0 | 100 |
| 69 | " | 6.5 | 87 |
| 70 | " | 7.0 | 78 |
| 71 | " | 8.0 | 52 |
| Example | | | |
| 72 | Isobutyric acid | 5.0 | 1 |
| 73 | " | 5.5 | 100 |
| 74 | " | 6.0 | 100 |
| 75 | " | 6.5 | 88 |
| 76 | " | 7.0 | 78 |
| 77 | " | 8.0 | 49 |

EXAMPLES 78 THROUGH 94 AND COMPARISON EXAMPLE 10

To each 2.5-ml aliquot of a suspension of washed cells ($1.8 \times 10^3$ U/ml) prepared as in Example 1, was added 2.5 ml of M/10 phosphate buffer containing a predetermined quantity of a stabilizer as shown in Table 5. The pH of the mixture was adjusted to 6.0 (6.5 for the suspension containing no stabilizer), and the resulting mixture was then left standing for 3 days in ice-cooled state.

The nitrile hydration activity levels were measured before and after each of the suspensions was left standing to calculate % residual activity. The results obtained are presented in Table 5.

TABLE 5

| Experimental Example | Stabilizer Added | Concentration (g/l) | % Residual Activity |
|---|---|---|---|
| Comparison Example | | | |
| 10 | None | — | 52 |
| Example | | | |
| 78 | Isobutyronitrile | 0.01 | 78 |
| 79 | " | 0.1 | 85 |
| 80 | " | 1.0 | 98 |
| 81 | " | 5.0 | 100 |
| 82 | " | 20 | 91 |
| Example | | | |
| 83 | Isobutyramide | 0.01 | 82 |
| 84 | " | 0.1 | 88 |
| 85 | " | 1.0 | 100 |
| 88 | " | 5.0 | 100 |
| 87 | " | 20 | 100 |
| 88 | " | 50 | 90 |
| Example | | | |
| 89 | Isobutyric acid | 0.01 | 80 |
| 90 | " | 0.1 | 83 |
| 91 | " | 1.0 | 100 |
| 92 | " | 5.0 | 97 |
| 93 | " | 20 | 95 |
| 94 | " | 50 | 87 |

Concentration: Concentration of the stabilizer in the solution left standing

EXAMPLES 95 AND COMPARISON EXAMPLE 11

50 ml of a suspension of washed cells prepared as in Example 1 was mixed with 50 ml of M/10 phosphate buffer (pH 6.5) containing 10 g/l of ammonium isobutyrate ($3.2 \times 10^3$ U/ml).

The resultant cell suspension was pressed in a French press (fabricated by Ohtake Seisakusho, Japan) to crush cells under a pressure of 1,000 to 1,500 kg G and then subjected to centrifugation (12,000 rpm, 30 minutes) to remove uncrushed cells and insolubles such as cell walls, whereby a cell extract, i.e. a crude enzyme solution, was obtained.

For comparison purposes, a similar cell suspension ($3.2 \times 10^3$ U/ml) which contained no ammonium isobutyrate was prepared and subjected to a French press treatment and centrifugation under similar conditions, whereby a control cell extract was obtained.

Both cell extracts were left standing for 3 days in ice-cooled state, and the nitrile hydration activity levels were measured before and after the extracts were left standing. The results are shown in Table 6.

TABLE 6

| Experimental Example | Ammonium Isobutyrate | Activity Before Being Left Standing (U/ml) | Activity After Being Left Standing (U/ml) | % Residual Activity |
|---|---|---|---|---|
| Example 95 | Added | $2.9 \times 10^3$ | $2.8 \times 10^3$ | 94 |
| Comparison Example 11 | None | $2.7 \times 10^3$ | $1.0 \times 10^3$ | 38 |

EXAMPLE 96 AND COMPARISON EXAMPLE 12

40 ml of washed cells (water content 75%) prepared as in Example 1, 4.5 g of acrylamide, 0.5 g of N,N'-methylenebisacrylamide, and 40 ml of M/20 phosphate buffer (containing 10 g/l of ammonium isobutyrate, pH 6.0) were mixed to form a homogeneous suspension. To this suspension were added 5 ml of a 5% aqueous solution of dimethylaminopropionitrile and 10 ml of a 1% aqueous solution of potassium persulfate, and the mixture was maintained at 10° C. for 30 minutes to cause polymerization. A mass of cell-containing gel obtained was crushed into small particles, which were thoroughly washed with M/20 phosphate buffer containing 5 g/l of ammonium isobutyrate, pH 7.0, whereby approximately 90 g of immobilized cells were obtained.

The washed, immobilized cells thus obtained were placed in the same buffer containing 5 g/l of isobutyric acid and left standing at 0° C. for 5 days.

For comparison purposes, the cells were immobilized and washed similarly but with the use of phosphate buffer containing no ammonium isobutyrate, and the resultant cells were left standing at 0° C. for 5 days.

The nitrile hydration activity levels of the gel samples were measured as follows before and after the respective immobilized cells were left standing.

1 g of immobilized gel was mixed with 5 g of acrylonitrile and 97 ml of M/20 phosphate buffer (pH 7.7), and the mixture was subjected to reaction at 0° C. for 20 minutes with stirring. The quantities of acrylamide in the respective reaction solutions were determined by gas chromatography. The results obtained are set forth in Table 7.

TABLE 7

| Experimental Example | Ammonium Isobutyrate | Quant. of AA produced (%) before cells were left standing | Quant. of AA produced (%) after cells were left standing |
|---|---|---|---|
| Example 96 | Immobilized with addition of isobutyric acid + Left standing in buffer containing isobutyric acid | 1.02 | 0.93 |
| Comparison Example 12 | None | 0.88 | 0.52 |

EXAMPLE 97 AND COMPARISON EXAMPLE 13

25 ml each of a cell extract containing ammonium isobutyrate and a control cell extract containing no ammonium isobutyrate prepared as in Example 95 and comparison Example 11 were mixed with 15 g each of DEAE-Cellulofine AM (supplied by Seikagaku Kogyo Co., Ltd., Japan) equilibrated with M/20 phosphate buffer (pH 7.7). The mixture was stirred at 0° C. for 90 minutes to immobilize the enzymes.

Both immobilized enzymes thus obtained were left standing for 3 days in ice-cooled state, and the nitrile hydration activity levels were measured before and after the enzymes were left standing. The results are presented in Table 8 in which the protein levels in the immobilized enzymes were determined in accordance with the procedure of Lowry et al.

TABLE 8

| Experimental Example | Ammonium Isobutyrate | Activity Before Being Left Standing | Activity After Being Left Standing | % Residual Activity |
|---|---|---|---|---|
| Example 97 | Added | 19.4 | 18.4 | 95 |
| Comparison Example 13 | None | 4.6 | 1.7 | 37 |

We claim:

1. A method for preservation of the nitrile hydration activity of nitrile hydratase produced by a microorganism of the genus Pseudomonas, of cells of microorganisms of said genus Pseudomonas, or of immobilized forms thereof, all having nitrile hydration activity, said method comprising admixing as a stabilizer at least one compound selected from the group consisting of nitriles, amides, and organic acids and salts thereof with a suspension or solution of said nitrile hydratase, of said microorganism cells, or of said immobilized forms thereof, and the concentration of nitrile, amide and organic acid or the salt thereof in the suspension or solution being in the range of from 0.01 to 50 g/l.

2. A method as claimed in claim 1, wherein the pH of the suspension or solution is in the range of from 5 to 8.

3. A method as claimed in claim 1, wherein the microorganism of the genus Pseudomonas is *Pseudomonas chlororaphis* B 23 (FERM BP-187) or Pseudomonas sp. PS 1 (FERM BP-188).

4. A method as claimed in claim 2, in which the pH of the suspension or solution is in the range from 5.5 to 7.

5. A method as claimed in claim 1, in which the compounds selected from nitriles, amides, and organic acids and salts thereof comprise compounds admixed and comprise:

(a) Aliphatic nitriles including acetonitrile, propionitrile and isobutyronitrile and corresponding amids and acids or salts thereof;

(b) Aminonitriles including glycine nitrile, α-aminopropionitrile and β-aminopropionitrile and corresponding amides and acids or salts thereof;

(c) Hydroxynitriles including lactonitrile, hydroxyacetonitrile and β-hydroxypropionitrile and corresponding amides and acids or salts thereof;

(d) Unsaturated nitriles including acrylonitrile and methacrylonitrile and corresponding amides and acids or salts thereof;

(e) Dinitriles including malononitrile, succinonitrile and adiponitrile and corresponding diamides and dibasic acids or salts thereof;

(f) Monocyanoamides and monocyanic acids including cyanoacetamide and cyanoacetic acid or salts thereof;

(g) Aromatic nitriles including benzonitrile and phenylacetonitrile and corresponding amides and acids or salts thereof.

(h) Heterocyclic nitriles including nicotinonitrile and isonicotinonitrile and corresponding amides and acids or salts thereof;

(i) Halogenated nitriles including chloroacetonitrile and β-chloropropionitrile and corresponding amides and acids or salts thereof; and (j) Acids having an aldehyde group including glyoxylic acid or salts thereof.

* * * * *